(12) United States Patent
Pratt

(10) Patent No.: US 8,579,993 B2
(45) Date of Patent: Nov. 12, 2013

(54) USE OF DYESTUFFS FOR DYEING KERATIN FIBERS AND COMPOSITIONS COMPRISING THE DYESTUFFS

(75) Inventor: Dominic Pratt, Gross-Gerau (DE)

(73) Assignee: KAO Germany GmbH, Darmstadt (DE)

(*) Notice: Subject to any disclaimer, the term of this patent is extended or adjusted under 35 U.S.C. 154(b) by 0 days.

(21) Appl. No.: 13/993,389

(22) PCT Filed: Dec. 23, 2011

(86) PCT No.: PCT/EP2011/073907
§ 371 (c)(1),
(2), (4) Date: Jun. 12, 2013

(87) PCT Pub. No.: WO2012/089645
PCT Pub. Date: Jul. 5, 2012

(65) Prior Publication Data
US 2013/0269121 A1 Oct. 17, 2013

(30) Foreign Application Priority Data
Dec. 27, 2010 (EP) .................................. 10016090

(51) Int. Cl.
*A61Q 5/10* (2006.01)
(52) U.S. Cl.
USPC ............ 8/405; 8/406; 8/408; 8/675; 132/202; 132/208
(58) Field of Classification Search
USPC .............. 8/405, 406, 408, 675; 132/202, 208
See application file for complete search history.

(56) References Cited

U.S. PATENT DOCUMENTS

| 2,628,963 A | 2/1953 | Laucius et al. |
| 2006/0031998 A1 | 2/2006 | De Boni et al. |
| 2006/0230549 A1* | 10/2006 | Hihara et al. ..................... 8/534 |
| 2009/0260165 A9 | 10/2009 | Brun et al. |

FOREIGN PATENT DOCUMENTS

| FR | 2 899 816 | 10/2007 |
| WO | 2006 108458 | 10/2006 |
| WO | 2006 114530 | 11/2006 |

OTHER PUBLICATIONS

STIC Search Report dated Aug. 1, 2013.*
International Search Report mailed Sep. 28, 2012.

* cited by examiner

*Primary Examiner* — Eisa Elhilo
(74) *Attorney, Agent, or Firm* — Norris McLaughlin & Marcus, P.A.

(57) ABSTRACT

Present invention relates to the use of a cationic anthrachinone dye for coloring keratin fibers, especially human hair, and compositions comprising the said dyestuffs. The object of the present invention is the use of dyestuff according to general structure

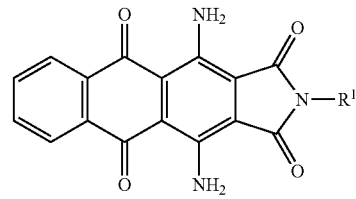

wherein $R_1$ is a group selected from $CH_3$, $CH_2OH$, $C_2H_2OH$, $C_4H_9$, $C_3H_6OC_2H_5$, $C_2H_4OCH_3$ and $C_3H_6OC_2H_4OCH_3$ for dyeing keratin fibers especially human hair.

11 Claims, No Drawings

USE OF DYESTUFFS FOR DYEING KERATIN FIBERS AND COMPOSITIONS COMPRISING THE DYESTUFFS

This application is a 371 application of PCT/EP2011/073907 filed Dec. 23, 2011, which claims foreign priority benefit under 35 U.S.C. §119 of European Application No. 10016090.2 filed Dec. 27, 2010.

Present invention relates to the use of a cationic anthraquinone dye for coloring keratin fibers, especially human hair, and compositions comprising the said dyestuffs.

Keratin fibers dyeing has been carried out with compositions comprising oxidative dyes as well as direct dyes. The disadvantageous of dyeing keratin fibers with direct dyes are mainly that the colors achieved are not long lasting, they are sensitive to the environmental effects, do not dye hair homogeneously. These drawbacks haven been addressed in many patent documents. These disadvantageous have been partly solved for some types of the dyestuffs but remained unsolved for blue dyes and therefore colors comprising blue dyestuffs still need to be optimized.

Present invention starts from the above problems and aims at providing blue dyestuffs especially suitable for dyeing keratin fibers for achieving long lasting, homogeneous dyeing of especially human hair. Additionally, the invention aims at providing dyeing compositions for keratin fibers especially human hair comprising the said blue dyestuffs.

The inventors of the present invention has surprisingly found out that the blue dyestuffs known from textile dyeing are excellent in achieving homogeneous long lasting colors on keratin fibers, especially human hair, and especially they are best suited for achieving violet colors or more generally achieving colour shades which requires a blue dyestuff.

The blue dyestuffs have been known form the patent publication WO 2005/005552 A1 and CN 101,671,492. The said documents list various types of dyes and disclose explicitly their suitability for dyeing textile. Nothing has been mentioned on dyeing keratin fibers, especially human hair.

Accordingly, the first object of the present invention is the use of dyestuff according to general structure

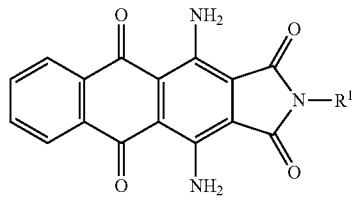

wherein $R_1$ is a group selected from $CH_3$, $CH_2OH$, $C_2H_2OH$, $C_4H_9$, $C_3H_6OC_2H_5$, $C_2H_4OCH_3$ and $C_3H_6OC_2H_4OCH_3$ for dyeing keratin fibers especially human hair.

Second object of the present invention is the use of composition comprising at least one dyestuff according to general structure given above for dyeing keratin fibers especially human hair.

Third object of the present invention is a kit for dyeing keratin fibers especially human hair comprising at least two compositions which may be applied onto keratin fibers especially human hair after mixing or one after another optionally after an intermediate rinsing off wherein at least one of the compositions comprise at least one dyestuff according to general structure given above.

Fourth object of the present invention is the use of at least one dyestuff according to general structure given above for achieving violet colours on keratin fibers especially human hair.

The preferred dyestuffs according to present invention are the following ones.

I
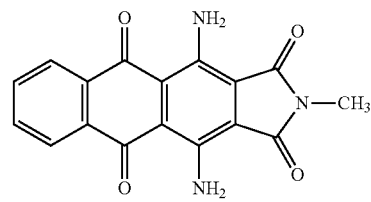

II
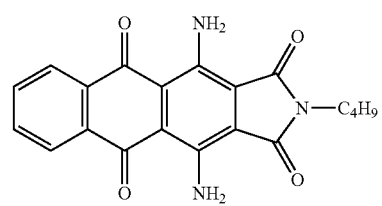

IV
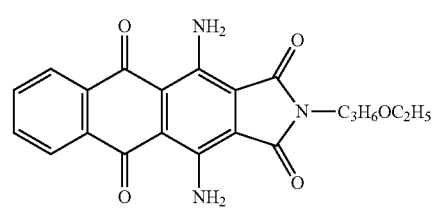

V
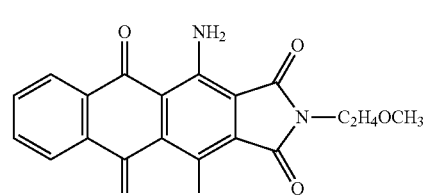

VI
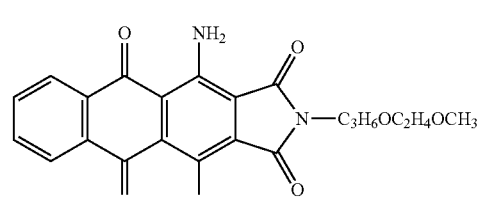

VII
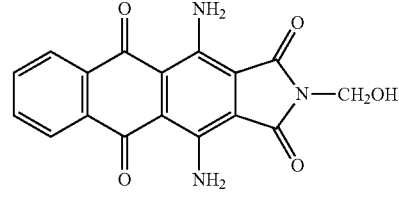

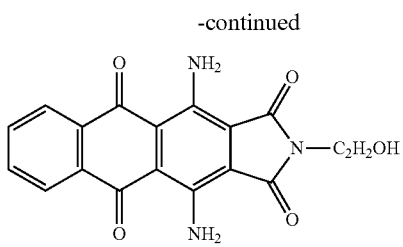

VIII

More preferred are according to structures I, V, VII and VIII and most preferred are I, VII and VIII.

Concentration of at least one dyestuff according to general structure given above is in the range of 0.0001 to 10%, preferably 0.001 to 7.5%, more preferably 0.01 to 5%, and most preferably 0.01 to 3% by weight calculated to total composition, prior to mixing with any other composition, especially with oxidizing composition. Further object of the present invention is a composition for dyeing keratin fibers especially human hair comprising at least one dyestuff according to above given general structure and at least one additional dye. In a further preferred embodiment of the present invention is the composition is an aqueous comprising and comprises at least 40% by weight calculated to total composition water.

Additional hair dye is selected from oxidative dye precursors and direct dyes. Suitable direct dyes are cationic, anionic and neutral nitro dyes.

Composition of the present invention comprises at least one oxidative dye precursor. Some examples are p-phenylenediamine, p-methylaminophenol and substituted p-phenylenediamines such as 2,5-diamino-toluene, 2-n-propyl or 2-ethyl-p-phenylenediamine, 2,6-di-methyl-p-phenylenediamine, 2-(2,5-diaminophenyl)ethanol, 1-amino-4-bis-(2'-hydroxy-ethyl)amino-benzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetramino pyrimidines, triaminohydroxy pyrimidines, diaminomono- and -dihydroxy pyrimidines, aminotriazines, 5-amino salicylic acid and 1,2,4-triamino benzene, or the water-soluble salts thereof. Preferably, at least one oxidative dyestuff precursor is selected from p-phenylenediamines, and substituted p-phenylenediamines such as 2,5-diamino-toluene, 2-(2,5-diaminophenyl)ethanol, 1-amino-4-bis-(2'-hydroxy-ethyl)amino-benzene, p-aminophenols such as p-methylaminophenol, pyrazols such as 1-hydroxyethyl-4,5-diaminopyrazole, pyrimidines such as tetramino pyrimidines, triaminohydroxy pyrimidines, and indols and indolines such as 6-hydroxyindole, 5,6-dihydroxyindole, 5,6-dihydroxyindoline and their respective salts.

More preferably at least one oxidative dye precursor is selected from p-phenylenediamine, 2,5-diamino-toluene, 2-(2,5-diaminophenyl)ethanol, 1-amino-4-bis-(2'-hydroxyethyl)amino-benzene, p-aminophenol, p-methylaminophenol, 1-hydroxyethyl-4,5-diaminopyrazole and their respective salts.

Total concentration of oxidative dye precursors are in the range of 0.01 to 10% by weight, preferably 0.05 to 7.5% by weight and more preferably 0.1 to 5% by weight, calculated to total composition prior to mixing with an oxidizing agent.

The composition according to the invention preferably comprises one or more additional coupling substance. Suitable ones are resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 3-amino-2-methylamino-6-methoxypyridine, 2-amino-3-hydroxypyridine, 2-dimethyl-amino-5-aminopyridine, 2,6-diaminopyridine, 5-amino-2-methylphenol, 2-methyl-5-hydroxyethylaminophenol, 2-methyl-5-amino-6-chlorphenol, 2-bis(2-hydroxyethyl)aminotoluene, 2-amino-5-methylphenol,α-naphthol, 4,6-dichlororesorcinol, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxybenzene, 5-amino-2-methoxyphenol, hydroxybenzomorpholine, 1,2,4-trihydroxybenzene, phenyl-methylpyrazolone, 3-amino-2,4-dichlorophenol, hydroxyethyl-3,4-methylenedioxyaniline, 2,6-dimethoxy-3,5-dimethylpyridine, 5-amino-4-chloro-2-methylphenol, hydroxypropyl-bis-(N-hydroxyethyl-p-phenylenediamine), 1-acetoxy-2-methylnaphthalene, 2,2"-methylenebis-4-aminophenol, 1,3-bis(2,4-diaminophenoxy)propane and/or their respective salts.

Preferably one or more couplers are selected from resorcinol, 2-methyl resorcinol, 4-chlororesorcinol, 3-amino-phenol, 1-methyl-2-hydroxy-4-aminobenzene, 2,6-dihydroxy-3,4-dimethylpyridine, 4-amino-3-methylphenol, 6-amino-3-methylphenol, 3-amino-2-methylamino-6-methoxypyridine, 2-amino-3-hydroxy-pyridine, 2-methyl-5-hydroxyethylaminophenol, 2-methyl-5-amino-6-chlorphenol, a-naphthol, 1,5-dihydroxy naphthalene, 2,7-dihydroxy naphthalene, 1-hydroxy-2-methyl naphthalene, hydroxybenzomorpholine, 1,2,4-trihydroxybenzene, phenylmethylpyrazolone, 3-amino-2,4-dichlorophenol, hydroxyethyl-3,4-methylenedioxyaniline, 2,6-dimethoxy-3,5-dimethylpyridine, 5-Amino-4-chloro-2-methylphenol, hydroxypropyl-bis-(N-hydroxyethyl-p-phenylenediamine), 1-acetoxy-2-methylnaphthalene, 2,2"-methylenebis-4-aminophenol, 1,3-bis(2,4-diaminophenoxy)propane and/or their respective salts.

More preferably, one or more additional couplers are selected from resorcinols such as resorcinol, 2-methyl resorcinol, 4-chlororesorcinol and/or m-aminophenols such as 3-amino-phenol, 1-methyl-2-hydroxy-4-aminobenzene, 2-methyl-5-hydroxyethylaminophenol, 2-methyl-5-amino-6-chlorphenol, 1,3-bis(2,4-diaminophenoxy)propane and/or their respective salts.

Total concentration of one or more coupling substances and their salts is in the range of 0.01 to 5% by weight, preferably 0.05 to 3% by weight and more preferably 0.1 to 2.5% by weight, calculated to total composition prior to mixing with an oxidizing agent.

Composition of the present invention comprises one or more direct dyes. Direct dyes suitable are cationic, anionic and/or nitro dyes.

Suitable non-limiting examples to cationic ones are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green, Basic Orange 31, 1, Basic Red 2, Basic Red 12 Basic Red 22, Basic Red 76 Basic Red 51, Basic Violet 1, Basic Violet 2, Basic Violet 3, Basic Violet 10, Basic Violet 14, Basic Yellow 57 and Basic Yellow 87.

Suitable non-limiting examples to anionic ones are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Suitable non-limiting examples to nitro dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Preferred direct dyes are cationic dyes such as Basic Orange 31, Basic Yellow 57 and Basic Yellow 87, anionic dyes such as Acid Yellow 1, Acid Yellow 23, Acid Yellow 3, D&C Orange No. 4, and Disperse Black 9 and nitro dyes such as HC Orange No. 1, HC Orange No. 2, Yellow No. 2, HC Yellow No. 4, HC Yellow No. 7, HC Yellow No. 9, HC Yellow No. 10, HC Yellow No. 13, picramic acid, 3-Nitro-4-aminophenol, 2-hydroxyethylpicramic acid, 3-Methylamino-4-nitrophenoxyethanol, 2-Nitro-5-glycerylmethylaniline, 4-Nitrophenyl aminoethylurea, Hydroxy-2-nitro-p-toluidine, and 2-Chloro-6-ethylamino-4-nitrophenol, and their respective salts.

More preferred direct dyes are cationic dyes such as Basic Orange 31, Basic Yellow 57 and Basic Yellow 87 and nitro dyes such as HC Orange No. 1, HC Orange No. 2, Yellow No. 2, HC Yellow No. 4, HC Yellow No. 7, HC Yellow No. 9, HC Yellow No. 10, HC Yellow No. 13, picramic acid, 3-Nitro-4-aminophenol, 2-hydroxyethylpicramic acid, 3-Methylamino-4-nitrophenoxyethanol, 2-Nitro-5-glycerylmethylaniline, 4-Nitrophenyl aminoethylurea, Hydroxy-2-nitro-p-toluidine, and 2-Chloro-6-ethylamino-4-nitrophenol, and their respective salts.

Most preferred are nitro dyes and especially those of HC Orange No. 1, HC Orange No. 2, Yellow No. 2, HC Yellow No. 4, HC Yellow No. 7, HC Yellow No. 9, HC Yellow No. 10, HC Yellow No. 13, picramic acid, 3-Nitro-4-aminophenol, 2-hydroxyethylpicramic acid, 3-Methylamino-4-nitrophenoxyethanol, 2-Nitro-5-glycerylmethylaniline, 4-Nitrophenyl aminoethylurea, Hydroxy-2-nitro-p-toluidine, and 2-Chloro-6-ethylamino-4-nitrophenol, and their respective salts.

Total concentration of one or more direct dyes is in the range of 0.001 to 10%, preferably 0.001 to 7.5%, more preferably 0.01 to 5% by weight calculated to total composition prior to mixing with oxidizing agent.

pH of the composition is in the range of 5 to 12, preferably 6 to 11 and more preferably 6.8 to 10, after mixing with an oxidizing agent.

Composition of the present invention can be mixed prior to application onto hair with a composition comprising at least one oxidizing agent. The preferred oxidizing agent is hydrogen peroxide at a concentration of 0.5 to 12% by weight. Other peroxides such as urea peroxide and melanin peroxide are also possible to use.

At the same time the subject of the present invention is process for colouring keratin fibres especially human hair wherein a composition comprising at least one dyestuff according to general structure given above and optionally at least one additional hair dye is mixed with an oxidizing composition comprising at least one oxidizing agent and applied onto hair and processed for 10 to 45 min at a temperature of 20 to 45° C. and rinsed off from hair.

The mixing ratio of the composition comprising at least one dyestuff according to general structure given above and optionally at least one additional hair dye and oxidizing composition comprising at least one oxidizing agent is preferably in the range of 3:1 to 1:3, by weight, more preferably in the range of 2:1 to 1:2, by weight, and in particular 1:1, by weight.

Composition of the present invention can comprise additionally substances customarily found in colouring compositions.

Compositions of the present invention can be in the form of solutions, dispersions, gels and emulsions. Most preferred is emulsion.

Coloring composition of present invention can comprise additionally in the base formulation fatty acids with 0 to 3 ethylenic bonds and with fatty acyl chain length of 12 to 22 C atom. Concentration of the fatty acids can be in the range of 0.1 to 10%, preferably 0.1 to 7.5% and most preferably 0.2 to 5% by weight calculated to the total composition, prior to mixing with oxidizing agent. Non-limiting examples are myristic acid, palmitic acid, behenic acid, steraic acid, oleic acid, linoleic acid. The most preferred fatty acid is oleic acid.

Coloring composition of the present invention comprise at least one fatty alcohol or mixture of fatty alcohols with the chain length of 14 to 22 C atoms which may be straight or branched, saturated or unsaturated. Examples to suitable fatty alcohols, without limiting the choice, are myristyl alcohol, cetyl alcohol, stearyl alcohol, behenyl alcohol, oleyl alcohol and cetostearyl alcohol, octyldodecanol. The most preferred is cetostearyl alcohol well known with its trade name Lanette O or as Lanette N in mixture with sodium cetearyl sulfate from Cognis. Total fatty alcohol content should be in the range of 1 to 20% by weight, calculated to total composition prior to mixing with an oxidizing agent.

Colouring compositions according to present invention comprises surfactants selected from anionic, amphoteric (or zwiterionic) and/or cationic surfactants as emulsifier or solubilizer. Cationic surfactants are as well used as hair conditioners in the colouring composition.

The preferred non-ionic emulsifiers are ethoxylated fatty alcohols with an alkyl chain of 12 to 24 C atoms and with number of ethoxyl groups of 2 to 50, preferably 10 to 30. Examples are ceteth-20, seteareth-30, palmeth-20, steareth-20, beheneth-20 etc. These compounds are named according to the fatty alcohol they are originating and number of ethoxyl groups is given at the end. These compounds are well known emulsifiers and found in any cosmetic ingredient book.

Further suited nonionic surfactants are, especially in mixture with fatty alcohol ethoxylates, for example, long-chain fatty acid mono- and dialkanolamides, such as coco fatty acid mono- or diethanolamide and myristic fatty acid mono or diethanolamide, stearic acid mono or diethanolamide.

Further nonionic surfactants suited again especially in admixture with fatty alcohol ethoxylates mentioned above are alkyl polyglucosides of the general formula $$R_2-O-(R_3O)_n-Z_x,$$

wherein $R_2$ is an alkyl group with 8 to 18 carbon atoms, $R_3$ is an ethylene or propylene group, Z is a saccharide group with 5 to 6 carbon atoms, n is a number from 0 to 10 and x is a number between 1 and 5.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are amineoxides. Such amineoxides are state of the art, for example $C_{12}$-$C_{18}$-alkyl dimethyl amineoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl) amineoxides, or also amineoxides with ethyleneoxide and/or propyleneoxide groups in the alkyl chain. Such amineoxides are on the market, for example, under the trade names "Ammonyx®", "Aromox®" or "Genaminox®".

Anionic surfactants suitable within the scope of the invention are in principal known from the cleansing compositions and may be present in an amount from 0.1 to about 10% by weight, calculated to the total composition prior to mixing with an oxidizing agent. Compatibility of anionic surfactant in the composition should be taken into account when choosing the type and the concentration.

These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates. Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula $$R_4-(C_2H_4O)_n-O-CH_2COOX,$$

wherein $R_4$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula $$R_4-\underset{\underset{O}{\|}}{C}-\underset{\underset{H}{|}}{N}-CH_2-CH_2-(C_2H_4O)_n-CH_2COOX$$

wherein $R_4$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants in a mixture.

An overview of the anionic surfactants suitable for the present invention can furthermore be found in the monography of K. Schrader, "Grundlagen and Rezepturen der Kosmetika", $2^{nd}$ Ed. (1989, Hüthig Buchverlag), pp. 595-600 and pp. 683 to 691.

As further surfactant component, the colouring compositions according to the invention can also contain amphoteric or zwitterionic surfactants, for example in an amount from about 0.5% to about 5%, preferably from about 1% to about 2.5% by weight, calculated to the total composition.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

Colouring composition can comprise cationic surfactants as emulsifier, solubilizer and/or conditioning ingredients according to the formula, $$R_8-\underset{\underset{R_{11}}{|}}{\overset{\overset{R_9}{|}}{N^+}}-R_{10} \quad X^-$$

where $R_8$ is a saturated or unsaturated, branched or non-branched alkyl chain with 8-22 C atoms or $$R_{12}CONH(CH_2)_n$$

where $R_{12}$ is saturated or unsaturated, branched or non-branched alkyl chain with 7-21 C atoms and n has typical value of 1-4 or $$R_{13}COO(CH_2)_n$$

where $R_{13}$ is saturated or unsaturated, branched or non-branched alkyl chain with 7-21 C atoms and n has typical value of 1-4, and $R_9$ is unsaturated or saturated, branched or non-branched alkyl chain with 1-22 C atoms or $R_{12}CONH(CH_2)_n$ or $R_{13}COO(CH_2)_n$ where $R_{12}$, $R_{13}$ and n are same as above.

$R_{10}$ and $R_{11}$ are lower alkyl chain with 1 to 4 Carbon atoms, and X is typically chloride, bromide, methosulfate.

Typical examples of those ingredients are cetyl trimethly ammonium chloride, stear trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

Form the above mentioned surfactants preferred are nonionic and anionic surfactants and their mixtures.

Total surfactant concentration is in the range of 0.5 to 15%, preferably 1 to 10%, more preferably 1 to 7.5% by weight calculated to total composition prior to mixing with an oxidizing agent.

Colouring composition can also contain cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 2, Polyquaternium 4, Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46, Polyquaternium 67, Polyquaternium 87.

Typical concentration range for any of the cationic conditioners mentioned above can be 0.01-5% by weight, preferably 0.03-2.5% by weight and more preferably 0.05-1.5% by weight.

Hair dyeing composition of the present invention preferably comprise an organopolysiloxane wherein at least one silicium atom is linked to an alkylene group having a heteroatom, in particular a nitrogen atom, with a poly-(N-acyl alkyleneimine) units of the formula

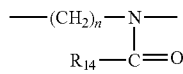

wherein n is a number from 1 to 5 and $R_{14}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

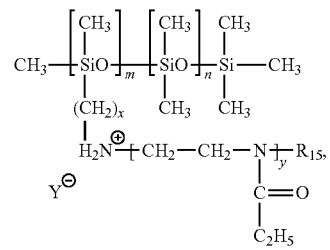

wherein m and n each are numbers from 20 to 10,000, in particular 50 to 7,000, especially 100 to 5,000, x is a number between 1 and 5, preferably 3, and y is a number from 5 to 30, $R_{15}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Coloring compositions according to the present invention can contain organic solvents as penetration enhancers and also as a solubilzers. Examples of such organic solvents are benzyloxy ethanol, benzyl alcohol, phenoxy ethanol, phenoxy isopropanol, methyl phenoxy ethanol, benzyl glycerol, N-benzyl formide, N-methylpyrrolidone, N-ethyl pyrrolidone, cinnamyl alcohol, phenethyl alcohol, p-methyl benzyl alcohol, butyl cellosolve, methyl carbitol, ethyl carbitol, propyl carbitol, butyl carbitol, diethyleneglycol, diethyl ether and dipropyleneglycol diethyl ether. Typically the concentration of those solvents can be in the range from 0.5% to 20%, preferably 0.5-15%, more preferably 0.5-10%, by weight calculated to the total composition, prior to mixing with oxidizing composition.

Colouring compositions according to the invention may comprise thickening agents. These are, for example, the various cellulose derivatives such as hydroxyalkyl celluloses, e.g. hydroxyethyl cellulose, hydroxypropyl cellulose, hydroxypropyl methyl cellulose, natural polysaccharides such as xanthan gum; guar gum and the alkoxylation products thereof in amounts from 0.1-5%, preferably 0.1-3% and most preferably 0.1-2% by weight calculated to the total composition prior to mixing with oxidizing composition and depending on the desired consistency thereof.

Optionally, the colouring composition of this invention can comprise further hair conditioning agents such as silicone oils either volatile or non-volatile, natural and synthetic oils. Among silicone oils those can be added to the colouring composition include dimethicone, dimethiconol, polydimethylsiloxane, DC fluid ranges from Dow Corning, natural oils such as olive oil, almond oil, avocado oil, weizenkeim oil, ricinus oil and the synthetic oils, such as mineral oil, isopropyl-myristate, palmitate, stearate and isostearate, oleyl oleate, isocetyl stearate, hexyl laurate, dibutyl adipate, dioctyl adipate, myristyl myristate and oleyl erucate.

Additional non-ionic conditioning agents may be polyols such as glycerin, glycol and derivatives, polyethyleneglycoles known with trade names Carbowax PEG from Union Carbide and Polyox WSR range from Amerchol, polyglycerin and polyethyleneglycol mono or di fatty acid esters.

Compositions may further comprise at least one ubiquinone of the formula

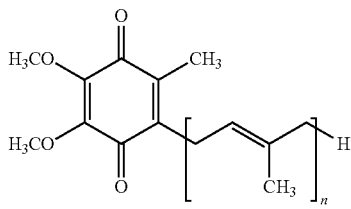

where n is a number between 1 and 10 at a concentration of 0.0001 to 1%, preferably from 0.0002 to 0.75%, more preferably from 0.0002 to 0.5% and most preferably from 0.0005 to 0.5% by weight, calculated to total composition, prior to mixing with oxidizing composition.

The composition comprises ubiquinone which is preferably selected from the ones where n is a number between 6 and 10 and more preferably it is ubiquinone 50 where n is 10, also known as Coenzyme Q10.

Composition can comprise at least one amino acid. At least one amino acid is comprised at a concentration of 0.01 to 10%, preferably 0.05 to 7.5% and more preferably 0.1 to 5% and most preferably 0.25 to 5% by weight calculated to total of each composition, prior to mixing with oxidizing composition.

Suitable amino acids are glycin, histidine, citrullin, asparagine, alanin, valin, leucin, isoleucin, pyrrolin, tryptophane, phenylalanine, methionine, serine, tyrosine, threonine and gluatamine. Preferably, the amino acid is selected from glycin, histidine, citrullin, asparagine, alanin, valin, leucin, isoleucin, pyrrolin, serine, tyrosine, threonine and gluatamine. More preferably, at least one amino acid is selected from glycin, histidine, asparagine, alanin, valin, leucin, pyrrolin, serine, tyrosine and gluatamine, and most preferably at least one amino acid is selected from glycin, asparagine, alanin, valin, leucin, and serine.

Composition can comprise further ceramide type of compound with the general formula

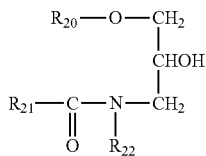

where $R_{20}$ and $R_{21}$ are independent from each other alkyl- or alkenyl group with 10 to 22 carbon atoms, $R_{22}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide.

Further optional ingredient are sterols, especially the phytosterols as preferred hair restructuring agents. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

Additionally, one or more natural oil may be incorporated into the compositions of the present invention. Suitable are such as olive oil, almond oil, avocado oil, wheatgerm oil, ricinus oil or their mixture. Concentration of natural oil should be 0.01 to 2.5%, preferably 0.01. to 1%, more preferably 0.05 to 0.5% by weight, calculated to total each composition, prior to mixing with oxidizing composition.

Furthermore, composition of the present invention is suitably provided to the users in the form of a kit. Accordingly, kit for dyeing keratin fibers especially human hair wherein it comprises at least two compositions which may be applied onto keratin fibers especially human hair after mixing or one after another optionally after an intermediate rinsing off wherein at least one of the compositions comprise at least one dyestuff according to general structure given in claim 1 and preferably another composition comprising at least one oxidizing agent.

Compositions of the present invention can further comprise ingredients customarily found in such compositions such as alkalizing agents, preservatives antioxidants, fragrances, reducing agents and chelating agents.

The following examples are to illustrate the present invention, but not to limit.

Example 1

| Base composition | |
|---|---|
| | % by weight |
| Octyldodecanol | 1.3 |
| Cetearyl alcohol | 1.0 |
| Oleyl alcohol | 2.6 |
| Sodium lauryl sulphate | 1.0 |
| Xanthan gum | 1.0 |
| Sodium sulfit | 0.5 |
| Ascorbic acid | 0.2 |
| Tetrasodium EDTA | 0.2 |
| Fragrance, preservative | q.s |
| Ammonia 25% | 8.0 |
| Water | q.s. to 100 |

| | Compositions | | | | | |
|---|---|---|---|---|---|---|
| Dyestuffs | I | II | II | IV | V | VI |
| Structure 8 | 0.5 | | | 0.5 | 0.5 | 0.5 |
| Structure 1 | | 0.5 | | | | |
| Structure 7 | | | 0.5 | | | |
| p-Toluenediamine | | | | 0.5 | | |
| p-Phenylenediamine | | | | | 0.5 | |
| p-Aminophenol | | | | | | 1.0 |
| m-Aminophenol | | | | 0.3 | | 0.3 |
| 4-Amino-2-hydroxytoluene | | | | | 0.3 | 0.4 |
| Resorcinol | | | | 0.2 | | |
| 2-amino-3-hydroxytoluene | | | | | 0.1 | |
| Sodium Picramate | | | | | | |
| HC Yellow 2 | | | | | | |
| 2-Amino-6-chloro-4-nitrophenol | | | | | | |
| Basic Red 51 | | | | | | |
| Basic Yellow 87 | | | | | | |
| HC Blue 17 | | | | | | |
| Color | Blue | Blue | Blue | Cool Brown | Violet Brown | Violet |

|  | Compositions | | | |
| --- | --- | --- | --- | --- |
| Dyestuffs | VII | VIII | IX | X |
| Structure 8 | 0.5 | 0.5 | 0.5 | 0.5 |
| Structure 1 | | | | |
| Structure 7 | | | | |
| p-Toluenediamine | 0.5 | | | |
| p-Phenylenediamine | | | | |
| p-Aminophenol | | | | |
| m-Aminophenol | 0.1 | | | |
| 4-Amino-2-hydroxytoluene | 0.1 | | | |
| Resorcinol | 0.2 | | | |
| 2-amino-3-hydroxytoluene | 0.1 | | | |
| Sodium Picramate | 0.05 | | | 0.2 |
| HC Yellow 2 | | | | 0.2 |
| 2-Amino-6-chloro-4-nitrophenol | 0.05 | | | 0.3 |
| Basic Red 51 | | 0.3 | | |
| Basic Yellow 87 | | 0.1 | | |
| HC Blue 17 | | | 0.3 | |
| Color | Ash Brown | Violet | Blue | Light Brown |

The above compositions I to X were mixed with a composition comprising 6% hydrogen peroxide at a weight ratio of 1:1 and applied onto hair and rinsed off from hair after processing of 30 min at ambient temperature. It was observed that hair was coloured homogeneously. The colours obtained are given below of each example.

The invention claimed is:

1. A method for dyeing keratin fibers comprising:
dyeing keratin fibers with a composition comprising at least one oxidizing agent and a dyestuff according to a general structure

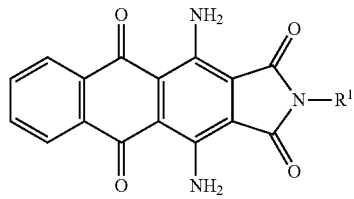

wherein $R_1$ is a group selected from $CH_3$, $CH_2OH$, $C_2H_2OH$, $C_4H_9$, $C_3H_6OC_2H_5$, $C_2H_4OCH_3$ and $C_3H_6OC_2H_4OCH_3$.

2. The method according to claim 1, wherein the method achieves violet colors on the keratin fibers.

3. The method according to claim 1, wherein the dyestuff is selected from the group of compounds consisting of

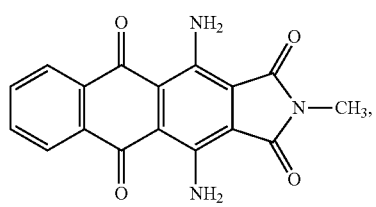

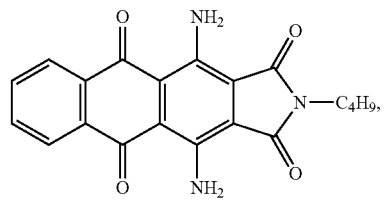

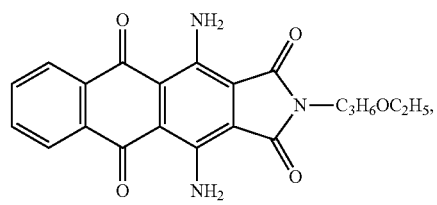

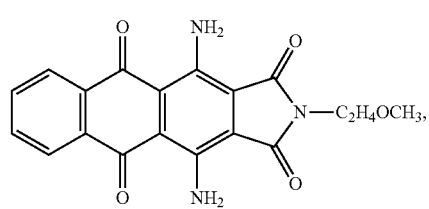

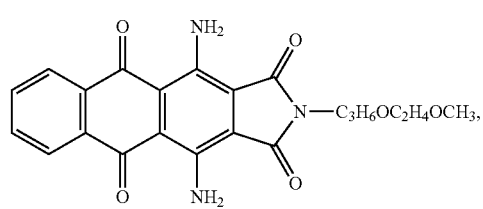

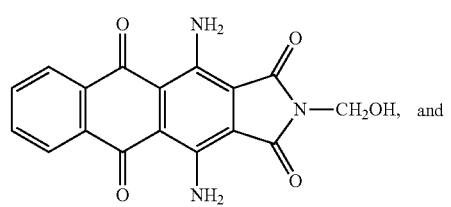

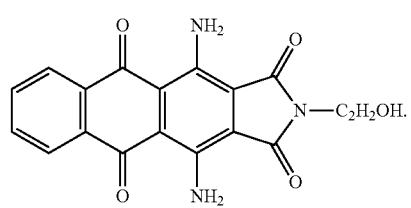

4. A composition for coloring keratin fibers, the composition comprising at least one oxidizing agent, at least one dyestuff according to a general structure

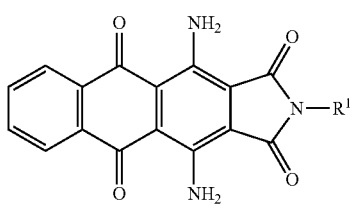

wherein $R_1$ is a group selected from $CH_3$, $CH_2OH$, $C_2H_2OH$, $C_4H_9$, $C_3H_6OC_2H_5$, $C_2H_4OCH_3$ and $C_3H_6OC_2H_4OCH_3$, and at least one additional dye.

5. The composition according to claim 4, wherein the composition is an aqueous composition and comprises at least 40% by weight water, calculated to total composition.

6. The composition according to claim 4, further comprising at least one direct dye selected from cationic, anionic and neutral nitro dyes.

7. The composition according to claim 4, further comprising at least one oxidative dye precursor.

8. The composition according to claim 7, further comprising at least one coupling substance.

9. The composition according to claim 4, further comprising at least one fatty alcohol and at least one surfactant.

10. The composition according to claim 4, further comprising at least one thickening agent.

11. A kit for dyeing keratin fibers comprising at least two compositions which may be applied onto the keratin fibers after mixing or one after another optionally after an intermediate rinsing off wherein at least one of the at least two compositions comprise the dyestuff according to general structure given in claim 4, wherein another composition of the at least two composition comprises at least one oxidizing agent.

* * * * *